(12) United States Patent
Sanderson (10) Patent No.: US 7,014,626 B2
(45) Date of Patent: Mar. 21, 2006

(54) DUAL-LUMEN PEEL-AWAY SHEATH INTRODUCER

(75) Inventor: David K. Sanderson, San Francisco, CA (US)

(73) Assignee: Endovascular Technologies, Inc., Santa Clara, CA (US)

(*) Notice: Subject to any disclaimer, the term of this patent is extended or adjusted under 35 U.S.C. 154(b) by 52 days.

(21) Appl. No.: 10/602,558

(22) Filed: Jun. 24, 2003

(65) Prior Publication Data

US 2004/0059298 A1 Mar. 25, 2004

Related U.S. Application Data

(63) Continuation of application No. 09/709,072, filed on Nov. 8, 2000, now Pat. No. 6,582,390.

(51) Int. Cl.
*A61M 5/00* (2006.01)

(52) U.S. Cl. ............. 604/171; 604/508; 604/165.1; 604/164.05

(58) Field of Classification Search ........... 604/93.01, 604/19, 98.02, 500, 523, 266, 43, 508, 164.05, 604/165.01; 128/772; 606/108, 165, 117; 600/585
See application file for complete search history.

(56) References Cited

U.S. PATENT DOCUMENTS

| | | | |
|---|---|---|---|
| 3,746,003 A | 7/1973 | Blake et al. | |
| 4,166,469 A | 9/1979 | Littleford | |
| 4,243,050 A | 1/1981 | Littleford | |
| 4,581,025 A | 4/1986 | Timmermans | |
| 4,947,864 A * | 8/1990 | Shockey et al. | 600/585 |
| 4,983,168 A | 1/1991 | Moorehead | |
| 5,064,414 A * | 11/1991 | Revane | 604/165.01 |
| 5,098,392 A * | 3/1992 | Fleischhacker et al. | 604/164.05 |
| 5,106,368 A | 4/1992 | Uldall et al. | |
| 5,125,904 A | 6/1992 | Lee | |
| 5,137,513 A | 8/1992 | McInnes et al. | |
| 5,250,033 A | 10/1993 | Evans et al. | |
| 5,320,602 A | 6/1994 | Karpiel | |
| 5,395,336 A | 3/1995 | Barclay et al. | |
| 5,409,469 A | 4/1995 | Schaerf | |
| 5,441,504 A | 8/1995 | Pohndorf et al. | |
| 5,571,161 A | 11/1996 | Starksen | |
| 5,618,267 A | 4/1997 | Palestrant | |
| 5,639,276 A | 6/1997 | Weinstock et al. | |
| 5,718,692 A | 2/1998 | Schon et al. | |
| 5,752,937 A | 5/1998 | Otten et al. | |

(Continued)

FOREIGN PATENT DOCUMENTS

WO    WO 00/74760 A2    12/2000

*Primary Examiner*—Henry Bennett
*Assistant Examiner*—L Fastovsky
(74) *Attorney, Agent, or Firm*—Fulwider Patton Lee & Utecht, LLP (57) ABSTRACT

A system and method for introducing medical devices within vasculature that incorporates a dual lumen introducer allowing a plurality of guidewires to be introduced without entanglement. The introducer further includes slits formed in the dual lumen introducer and a dilator or an inner member with grooves that facilitate easy removal of the introducer and dilator from vasculature. The dual lumen introducer maintains separation between guidewires. The slits in the dual lumen introducer and the dilator grooves allow removal from the guidewires by slipping the device off the guidewires without retracting them the entire guidewire length. A peel-away sheath protects the vasculature from the guidewires, prevents the dilator from slipping off the guidewires, and maintains access to an expanded vessel for the introduction of medical devices.

16 Claims, 7 Drawing Sheets

U.S. PATENT DOCUMENTS

| | | |
|---|---|---|
| 5,776,111 A | 7/1998 | Tesio |
| 5,873,854 A | 2/1999 | Wolvek |
| 5,885,217 A | 3/1999 | Gisselberg et al. |
| 6,022,342 A | 2/2000 | Mukherjee |
| 6,027,480 A | 2/2000 | Davis et al. |
| 6,080,141 A | 6/2000 | Castro et al. |
| 6,083,207 A | 7/2000 | Heck |
| 6,095,990 A | 8/2000 | Parodi |
| RE36,857 E | 9/2000 | Euteneuer et al. |
| 6,152,909 A * | 11/2000 | Bagaoisan et al. ........... 604/523 |
| 6,159,195 A * | 12/2000 | Ha et al. .................... 604/500 |
| 6,258,058 B1 | 7/2001 | Sanfillippo |
| 6,440,161 B1 | 8/2002 | Madrid et al. |
| 6,682,519 B1 * | 1/2004 | Schon ........................ 604/508 |
| 6,682,536 B1 | 1/2004 | Vardi et al. |
| 2001/0044595 A1 * | 11/2001 | Reydel et al. ............ 604/98.02 |
| 2001/0044622 A1 | 11/2001 | Vardi et al. |

* cited by examiner

DUAL-LUMEN PEEL-AWAY SHEATH INTRODUCER

This application is a continuation of application Ser. No. 09/709,072, filed Nov. 8, 2000 now U.S. Pat. No. 6,582,390.

BACKGROUND OF THE INVENTION

This invention relates generally to a system and method for introducing medical devices into vasculature. In particular, the present invention is concerned with the parallel introduction of a second guidewire into vasculature of the body, into which one guidewire has already been introduced, in such a way as to prevent entanglement of the guidewires. The present invention is also directed to facilitating removal of a dilator from vasculature without having to retract it the entire guidewire length. As used herein, the term "proximal" refers to a location on the device closest to the clinician using the device. Conversely, the term "distal" refers to a location on the device farthest from the clinician and closest to the patient into whom the device is to be inserted.

For many medical purposes it is important to introduce devices, both permanently and for temporary diagnostic purposes, through the skin and underlying tissue layers into blood vessels or other locations inside the body of a patient. One of the earliest methods used to place such devices into the body involved cutting an opening in the body, inserting the device and then either closing the wound around the device or after the device has been removed. Because of the high skill and specialized medical facilities required to accomplish such a procedure, as well as the risk of trauma and infection, a need arose to develop less-invasive methods.

It is well established that percutaneous methods, involving creating a small opening in tissue and the use of devices such as dilators to gain access to vasculature, allow for the introduction of medical devices into the body without some of the risks associated with earlier methods. In particular, the size of the cut down employed to gain access to a vessel could be minimized. However, the use of a dilator alone requires that the medical device be inserted quickly once the dilator is removed. Additionally, such systems can also have associated therewith the risk of bleeding, damage to the medical device, or damage to the body during insertion.

It has also been established that the use of a thin-walled peel-away introducer sheath secured to a dilator at its proximal end provides for the introduction of medical devices while reducing some of the risks associated with dilator-only systems. The peel-away sheath allows removal of the dilator while leaving the sheath inside the body, thereby maintaining access to the expanded tissue opening and providing a conduit for the medical device. Additionally, such systems can reduce the tendency of the dilator to migrate proximally when it is initially introduced through the skin and subcutaneous tissue.

One drawback of conventional introducer devices becomes apparent when more than one guidewire is required for a particular procedure. When more than one guidewire is introduced into a single vessel, there is a possibility that they may become entangled. Another drawback of present devices is that removal of the dilator requires it to be retracted along the entire guidewire.

Accordingly, there is a need for a device and method that facilitates the insertion of more than one guidewire into vasculature while avoiding the potential for entanglement as well as permits a dilator to be removed without having to retract it along the entire guidewire length. The present invention fulfills these and other needs.

SUMMARY OF THE INVENTION

Briefly, and in general terms, the present invention is directed to a new and improved device and method for introducing medical devices within the vasculature of the body. The novel features of the present invention include a dual lumen introducer and inner member with longitudinally extending grooves. The dual lumen introducer allows a second wire (for example, a guidewire or a medical device manipulation wire) to be introduced into a single vessel without becoming entangled with a first guidewire already introduced. The introducer can be used with more than two wires and with other types of diagnostic or therapeutics devices, for example angiographic catheters. The use of an inner member or dilator with grooves formed along an outer surface thereof allows the same to be removed without having to retract it along the entire guidewire length. In other words, the guidewire slips easily out of the grooves.

In one aspect, the dual lumen introducer of the present invention embodies a hub, an inner member or dilator with longitudinally extending grooves, and a tear-away sheath. In use, the introducer device is threaded over a guidewire which has been inserted into the vasculature either percutaneously via a needle or other conventional surgical techniques. The introducer is then employed to introduce another wire(s) into the patient's vasculature. Thereafter, the dilator is removed from the vasculature, leaving the sheath to maintain access to the vessel. Alternatively, the sheath can be peeled apart allowing the wires to be released from the dilator before the dilator is removed from the vasculature. The sheath can be removed as necessary by pulling the sheath proximally and simultaneously peeling it apart. Medical devices can then be introduced into the vasculature via the guidewires.

In another aspect of the invention, the hub includes two or more lumens; one for backloading the device over a guidewire already inserted into the vasculature and others for facilitating the introduction of another guidewire(s) into the vasculature. These lumens operate to separate the guidewires and prevent the guidewires from becoming crossed or entangled. It is contemplated that the dilator be bonded to the hub. The sheath, which is slid over the dilator, has a handle at its proximal end which locks to the hub. An internal bore of the sheath and the longitudinal extending grooves form lumens for receiving the guidewires.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As shown in the exemplary drawings and for purposes of illustration, the invention is embodied in a device and method for introducing medical devices within vasculature. In one aspect, the introducer includes a hub, a peel-away sheath, and an inner member or dilator, and has associated therewith a method of introducing the same into vasculature. The present invention involves facilitating the introduction of a plurality of wires (for example, two guidewires or a guidewire and a medical device manipulation wire) within vasculature and the expedient removal of the dilator of the invention from within vasculature. It is contemplated that the present invention includes a hub with multiple lumens which operates to separate wires or other therapeutic or diagnostic devices to thereby avoid entanglement and a dilator configured with longitudinally extending grooves which facilitate its easy removal from vasculature.

Figure 1:
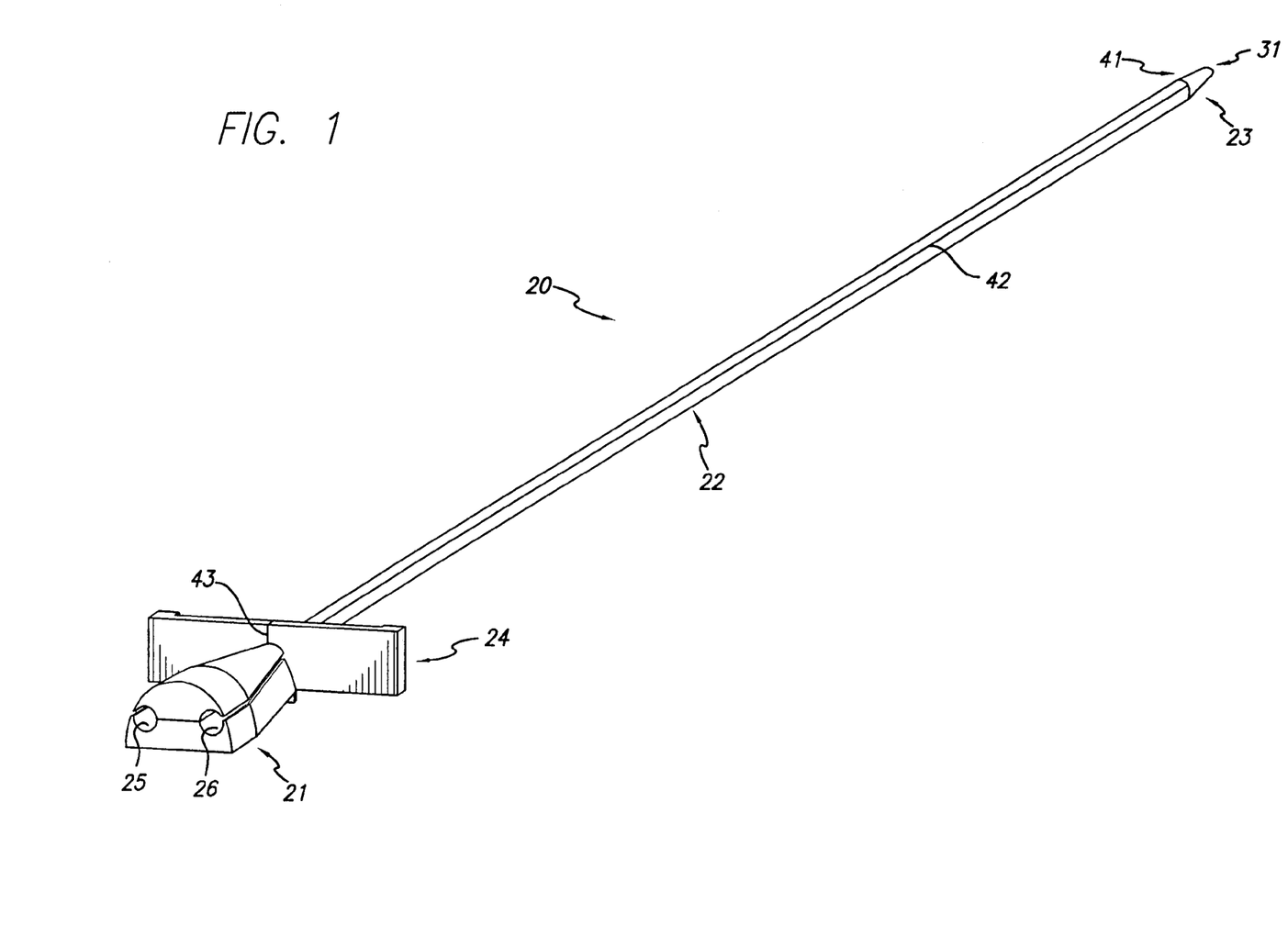
FIG. 1 is a perspective view of a system embodying the invention.

Referring to FIG. 1, the introducer 20 includes a hub 21 with dual lumens 25, 26, a dilator or inner member 23, and a generally tubular sheath 22 with sheath handle 24. The proximal end of the dilator 23 is joined (not shown) to the hub 21. The sheath 22 is slid over the dilator 23 and the sheath handle 24 is locked to the hub 21. In a preferred embodiment, the sheath 22 extends distally along the dilator 23 to a point 41 just proximal of the terminal end 31 of dilator 23. Additionally, the sheath 22 includes a pair of weakened areas consisting of longitudinally extending perforations or recesses 42 that are spaced 180° degrees circumferentially apart on the sheath. Alternatively, a single weakened area could be used. The perforations or recesses 42 on the sheath extend longitudinally through a circular knob 28 (See FIGS. 2A and 2B) at the proximal end of the sheath where it is bonded to the sheath handle 24 and also along a midline 43 of the sheath handle 24. As will be described below, it is intended that the sheath handle 24 can be fractured about a midline 43 and oppositely directed forces applied so that the sheath splits along the perforation or recess 42.

Figure 2A:
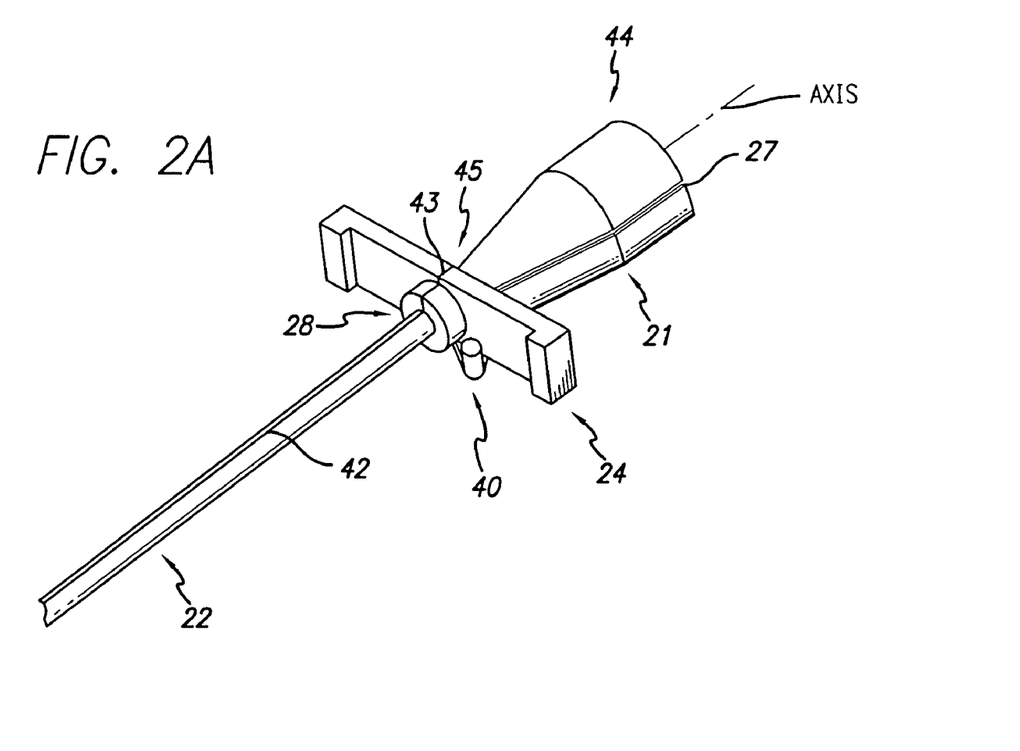
FIGS. 2A and 2B are perspective views of the proximal end of the system.
Figure 2B:
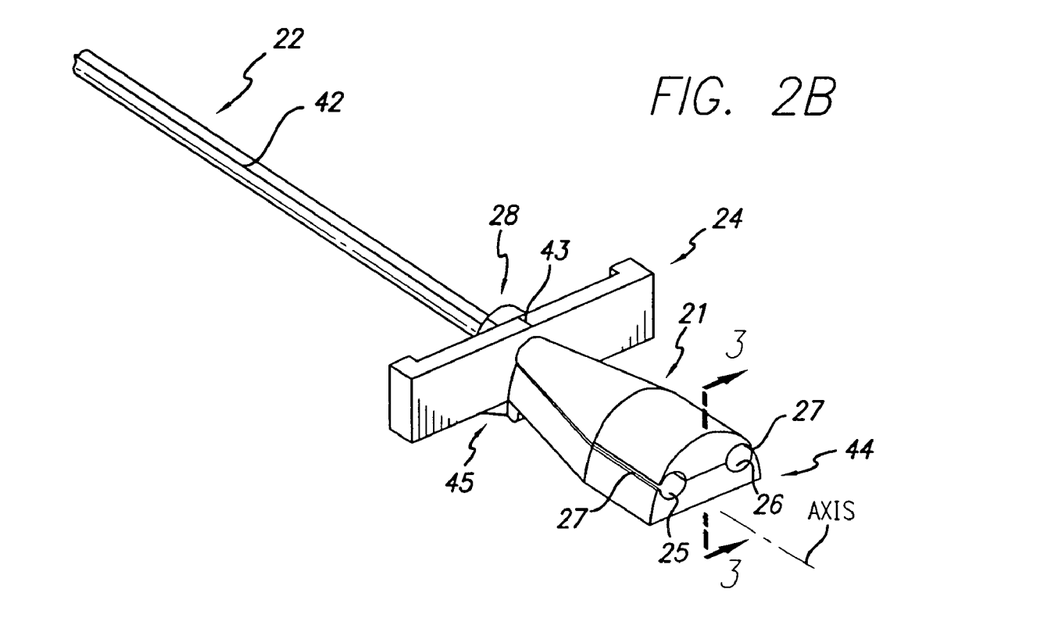

Referring now to FIGS. 2A and 2B, the introducer 20 further includes a locking post 40. Additionally, the sheath 22 further includes the circular knob 28 at its proximal end. When the sheath is slid over the dilator 23, the sheath handle 24 is held generally perpendicular to a longitudinal axis of the dilator 23 and locked to the hub 21 by turning the sheath handle 24 and placing it proximal to the locking post 40. The circular knob 28 operates to facilitate securing the sheath handle 24 against the locking post 40.

With the sheath 22 locked to the hub 21, the device can be introduced into the vasculature as a single assembly. When the sheath 22 is unlocked from the hub 21, for example by turning the sheath handle 24 in a counter-clockwise direction, the hub 21 and dilator 23 can be maneuvered as a separate unit from the sheath 22, thereby allowing the dilator 23 to be removed from the vasculature independent of the sheath 22. The sheath 22 can be peeled-away, as stated, by snapping the ends of the sheath handle 24 (See FIG. 19).

In one aspect of the invention, the dual lumens 25, 26 of the hub 21 each have a slit 27 extending in a distal direction. The slits 27 allow the wires (not shown) to be expediently disengaged from the hub 21 by pulling them in a direction that is transverse to the hub 21.

Figure 3:
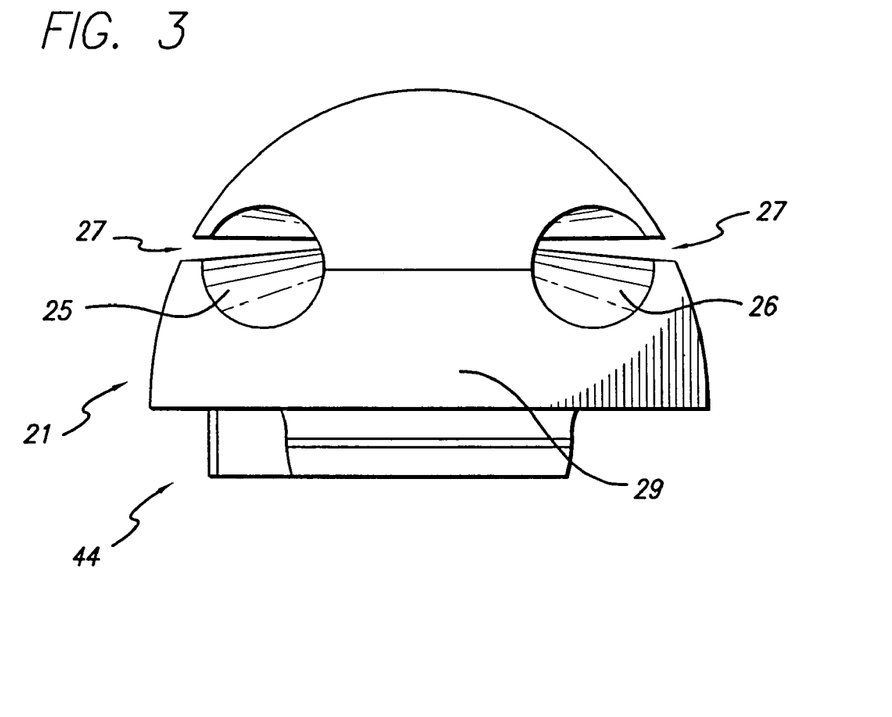
FIG. 3 is a cross-sectional view along the line 3—3 of FIG. 2B.
Figure 4A:
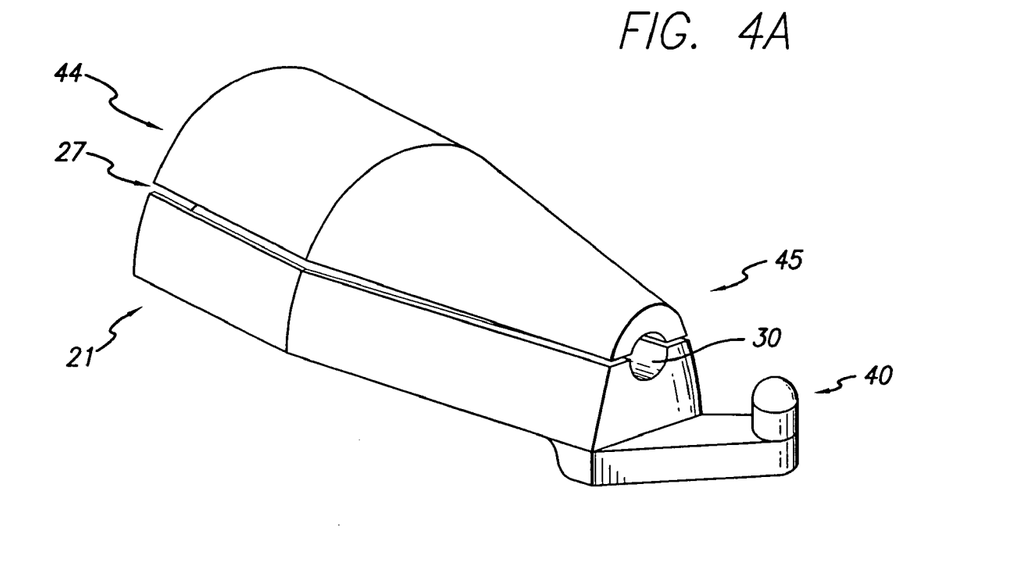
FIGS. 4A and 4B are perspective views of a hub detached from the remainder of the invention.
Figure 4B:
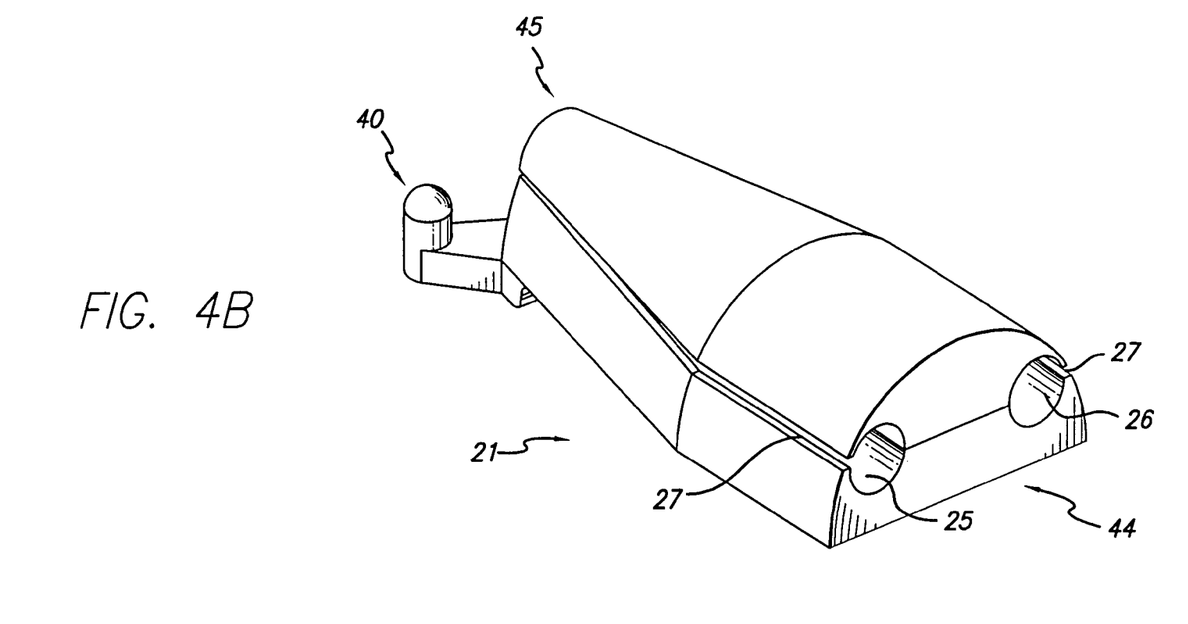
Figure 5:
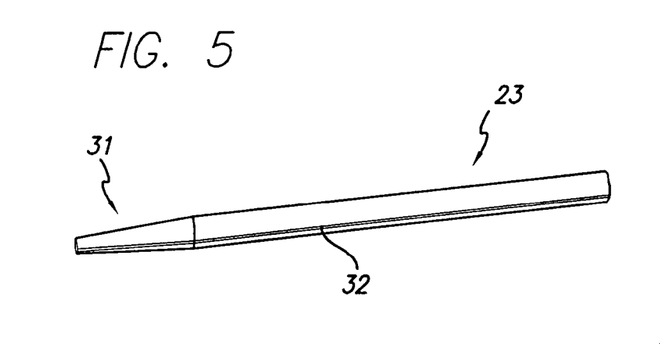
FIG. 5 is a perspective view of a the dilator of the invention without the sheath attached.
Figure 6:
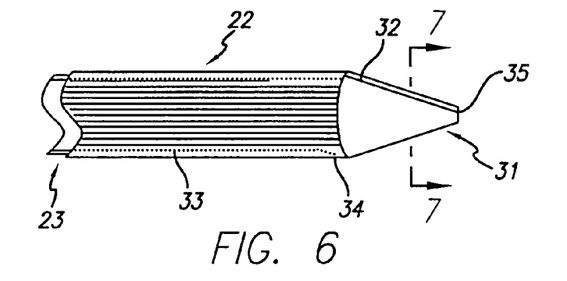
FIG. 6 is a top view depicting one preferred embodiment of the terminal end of the dilator with the sheath attached.
Figure 7:
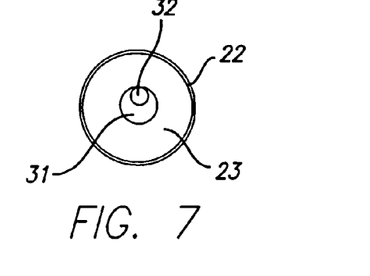
FIG. 7 is a cross-sectional view of the dilator along line 7—7 of FIG. 6.

Referring now to FIGS. 3 to 4B, the dual lumens 25, 26 are separated at a proximal end 44 of the hub 21 by a center wall 29 and converge to a single lumen 30 at a distal end 45 of the hub 21 where dilator (not shown) is joined to the hub 21. The dilator maintains separation of the wires at the distal end of the hub.

In a preferred embodiment of the invention, each of the dual lumens 25, 26 can accommodate a wire up to approximately 0.035″ (0.89 mm) in diameter. Moreover, the sheath length is contemplated to be about 45 cm with a diameter of about 10F (3.3 mm). The dilator itself can be from 16 to 45 cm long. The hub, sheath and dilator are made of medical grade polymers, such as a polycarbonate or polyurethane material. It is anticipated that alternate embodiments of the invention could have more than two lumens, with adjustments in allowable wire or other therapeutic or diagnostic device diameter.

As shown in FIGS. 5 to 13, the dilator or inner member 23 contains two grooves 32, 33 that run nearly the entire length of the dilator 23. When the sheath 22 is placed over the dilator 23, its inner wall forms a lumen with each of the grooves 32, 33 for receiving a wire (not shown). When the sheath 22 is removed or the dilator 23 retracted from the sheath 22, the grooves 32, 33 permit the dilator 23 to be slipped off the wires without having to retract the dilator 23 the entire length of a particular wire. The groove 32 narrows and is much smaller in the tapered terminal end 31 of the dilator 23 such that the tapered terminal end 31 does not easily slip off a wire as with other portions of the groove, but must be peeled off. In a preferred embodiment (FIGS. 6 and 7), one of the grooves 32 extends to a point 35 at the tapered terminal end 31 of dilator 23, while the other groove terminates at a point 34 proximal to the tapered terminal end 31 of the dilator 23. In this instance, the dilator tip forms a lumen for the primary guidewire. The dilator tip forming the lumen is scored to allow removal from the guidewire.

Figure 8:
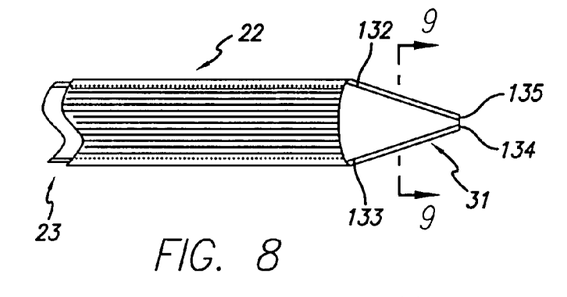
FIG. 8 is a top view depicting an alternate embodiment of the terminal end of the dilator with the sheath attached.
Figure 9:
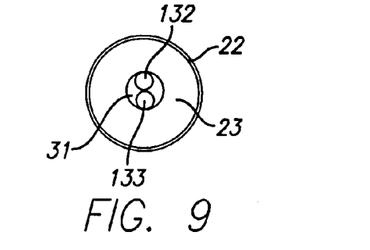
FIG. 9 is a cross-sectional view of the dilator along line 9—9 of FIG. 8.
Figure 10:
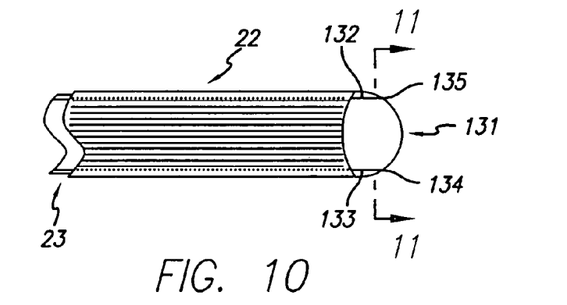
FIG. 10 is a top view depicting yet another alternate embodiment of the terminal end of the dilator with the sheath attached.
Figure 11:
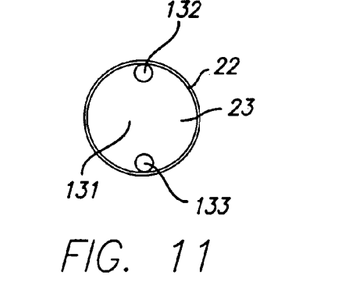
FIG. 11 is a cross-sectional view of the dilator along line 11—11 of FIG. 10.
Figure 12:
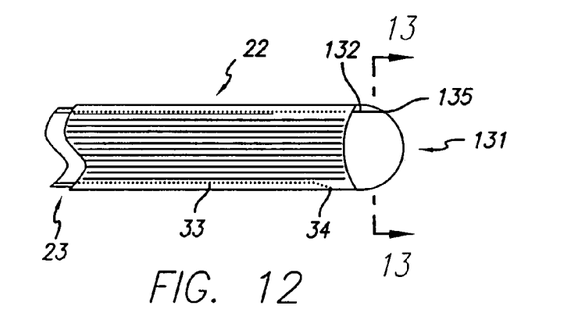
FIG. 12 is a top view depicting still yet another alternate embodiment of the terminal end of the dilator with the sheath attached.
Figure 13:
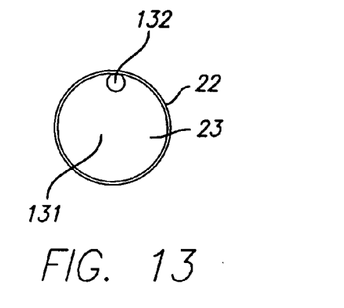
FIG. 13 is a cross-sectional view of the dilator along line 13—13 of FIG. 12.

In an alternate embodiment of the invention (FIGS. 6–9), the terminal end 31 of the dilator 23 can be made more flexible than the shaft so that the tip is atraumatic. Additionally, in alternative embodiments, the dilator 23 may have as many grooves as necessary for the intended application. Moreover, as shown in FIGS. 8 and 9, both grooves 132, 133 can be configured to extend to points 134, 135, respectively, near the terminal end of the dilator 23. FIGS. 10 to 13 show alternate embodiments in which the terminal end 131 of the dilator 23 is rounded rather than tapered.

Figures 14, 15, 16:
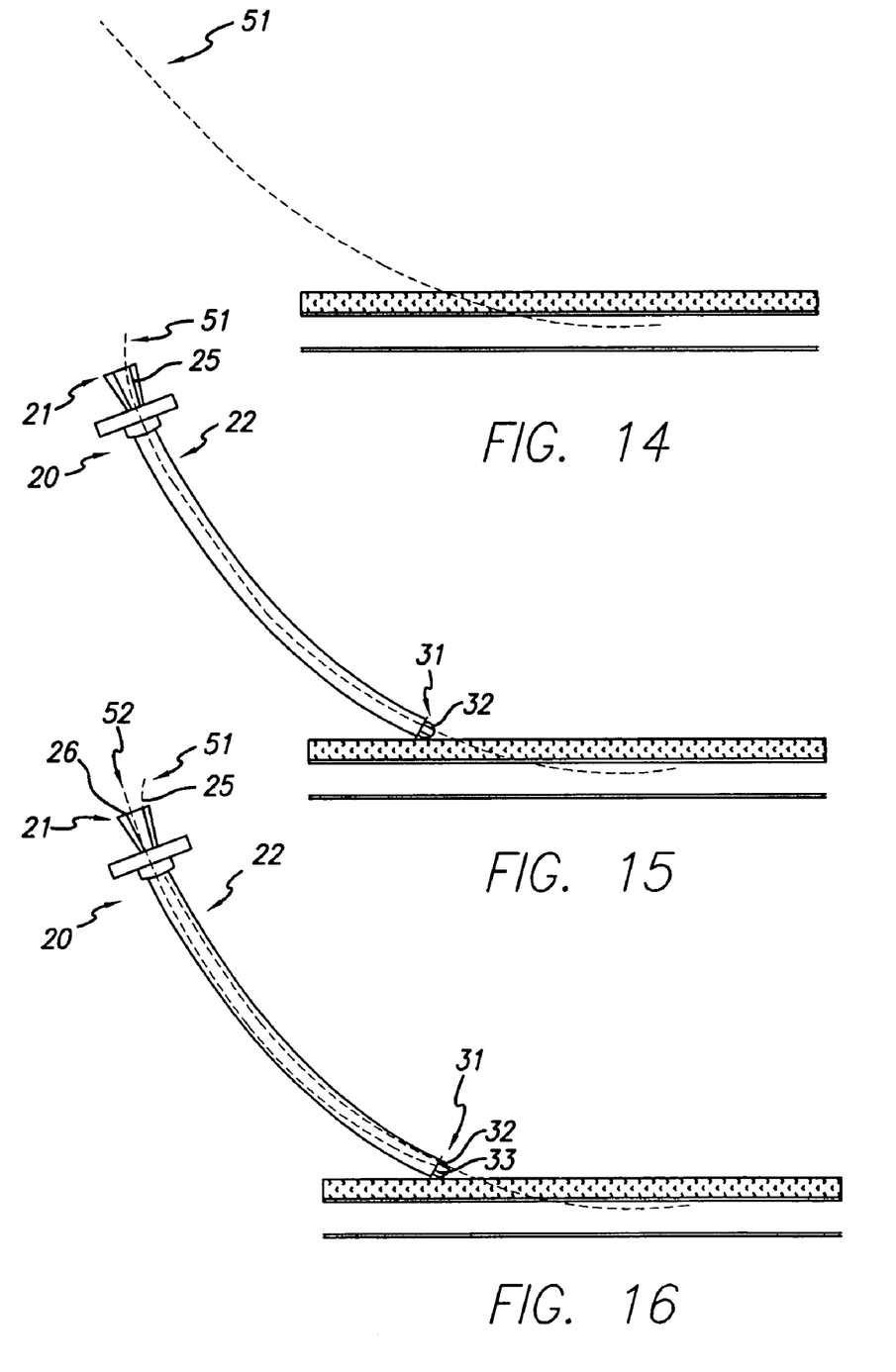
FIG. 14 is a partial cross-sectional view depicting a guidewire inserted in the vasculature of the body.
FIG. 15 is a partial cross-sectional view depicting a dual lumen introducer of the present invention back loaded on a guidewire inserted in the vasculature of the body.
FIG. 16 is a partial cross-sectional view depicting a second wire introduced into the dual lumen introducer shown in FIG. 15.
Figure 17:
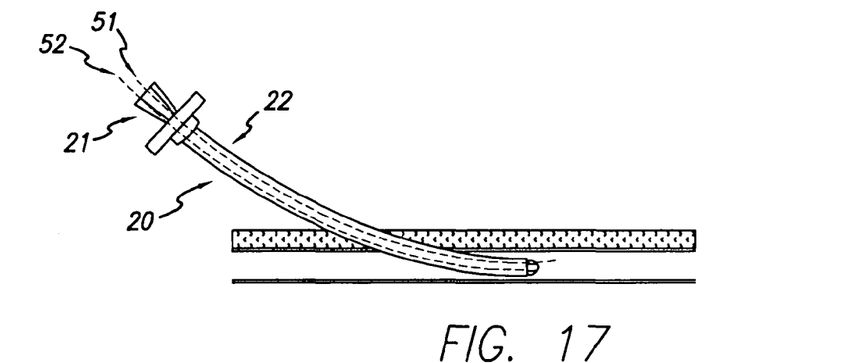
FIG. 17 is a partial cross-sectional view depicting the dual lumen introducer of FIG. 16 being advanced within vasculature of the body.

Turning now to FIGS. 14 to 19, steps in one anticipated use of the invention is shown. Using a standard percutaneous technique, a guidewire 51 is placed within vasculature and advanced to a target site using fluoroscopy. With the guidewire 51 extending from the body as shown in FIG. 14, the dual lumen peel-away introducer 20, with the sheath 22 locked to the hub 21, is then fed over the guidewire 51. To accomplish this, the guidewire 51 is placed within the dilator groove 32 and through the lumen created by the inner wall of the sheath 22 and dilator groove 32 until the guidewire emerges proximally from one of the dual lumens 25 of the hub 21 as shown in FIG. 15. The second guidewire 52 is then inserted into the other of the dual lumens 26 of the hub 21 and advanced distally through the lumen created by the inner wall of the sheath 22 and dilator groove 33 until it reaches the distal end of the dilator 31 as shown in FIG. 16. The dual lumen peel-away introducer 20 and second guidewire 52 are then advanced simultaneously along the first guidewire 51 to a desired position in the vasculature as shown in FIG. 17. Alternatively, the introducer can be advanced to the desired position before the second guidewire 52 is advanced through the second lumen 26. Significantly, the introducer 20 is designed to have a length that is sufficient to extend from an entry point of a patient's vasculature to the aortic bifurcation, for example.

Figure 18:
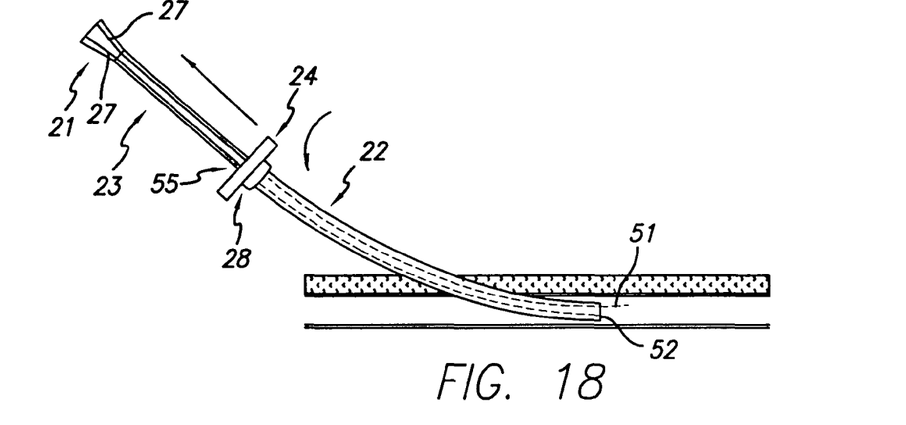
FIG. 18 is a partial cross-sectional view depicting the dilator and hub of the invention being withdrawn from the vasculature.

Once the desired position in the vasculature is reached, the hub 21 and dilator 23 can be removed, leaving the sheath 22 in place in the vasculature. It is to be recognized, however, that depending on the application, the sheath 22 can be removed first leaving the dilator 23 in place in the vasculature. To withdraw the sheath 22, the sheath handle 24 can be moved in a counterclockwise direction to unlock it from the hub lock 40. Then, holding the sheath handle 24 and guidewires 51, 52 steady, the hub 21 is pulled proximally to retract the dilator 23 as shown in FIG. 18. Alternatively, the entire device may be retracted from the vasculature and removed from the wires outside the body.

When the terminal end 31 of the dilator 23 exits the proximal end 55 of the sheath handle 24, the dilator 23 is removed by sliding it off the first guidewire 51 via groove 32 and off the second guidewire 52 via groove 33. The guidewires 51, 52 can be removed from the hub 21 by pulling them transversely through the slits 27. The first guidewire 51 is separated from the dilator tip through the score at the tip. The two guidewires 51, 52 are now free to be utilized for subsequent medical steps.

Figure 19:
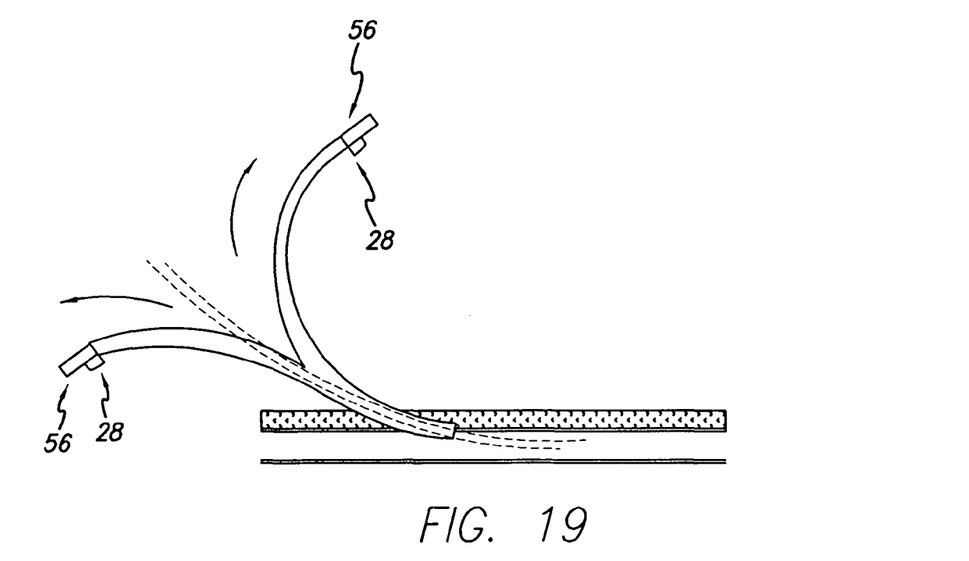
FIG. 19 is a partial cross-sectional view depicting removing the peel-away sheath of the invention from the vasculature.

The sheath 22 can be removed as desired by snapping down on the tabs 56 that form the sheath handle 24 and circular knob 28 while the sheath is pulled from the vasculature, thereby causing it to fracture into two pieces. By continuing to apply oppositely directed forces to the fractured pieces of the handle 24, the sheath 22 will split along the pair of perforations or recesses 42 to thereby peel-away from the guidewires 51, 52 as shown in FIG. 19.

As will be readily apparent to one of skill in the design of medical device introduction systems, the medical device introduction system of the present invention may be incorporated in various forms of dilators and peel-away sheaths. In addition, while the foregoing discussion of the embodiment of the device introduction system illustratively employed two wires, a greater or lesser number of wires may be accommodated. Furthermore, the steps in the anticipated procedure illustrated in FIGS. 14 to 19 may be altered if it is desired to remove the sheath before the dilator is retracted from the vasculature.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Moreover, the introducer of the present invention can be adapted to facilitate the insertion of a myriad of medical devices into vasculature for numerous different uses such as inserting leads in a cardiology application.

Accordingly, it is not intended that the invention be limited, except as by the appended claims.

What is claimed is:

1. A system for introducing medical devices within vasculature, comprising:
   a first medical device;
   a second medical device;
   an elongate member having a length, the elongate member including a structure to separate the first medical device from the second medical device along the length of the elongate member; and
   a sheath, the sheath extending substantially the length of the elongate member and overlaying the structure to separate the first medical device from the second medical device;
   wherein the elongate member further comprises a proximal end, a terminal end, and at least one groove extending longitudinally from the proximal end to proximate the terminal end.

2. The system of claim 1, wherein the sheath is sized to receive the elongate member.

3. The apparatus of claim 1, wherein the elongate member operates as a dilator.

4. The apparatus of claim 1, the elongate member further comprising a proximal end, a terminal end, and a first groove and a second groove each extending longitudinally along the elongate member.

5. The apparatus of claim 2, the elongate member further comprising a proximal end and a distal end, and a lock attached to the proximal end, the lock being configured to lock the introducer sheath to the inner member.

6. The apparatus of claim 2, the introducer sheath further comprising a distal end and a proximal end, the proximal end defining a handle.

7. The apparatus of claim 6, wherein the handle is adapted to be fractured into two pieces.

8. The apparatus of claim 1, the introducer sheath further comprising at least one longitudinally extending perforation along which the sheath can be split.

9. A system for introducing medical devices within vasculature, comprising:
   a first medical device;
   a second medical device;

an elongate member having a length, the elongate member including structure to separate the first medical device from the second medical device along the length of the elongate member; and a sheath, the sheath extending substantially the length of the elongate member and overlaying the structure to separate the first medical device from the second medical device;

the elongate member further comprising a proximal end, a terminal end, and a first groove and a second groove each extending longitudinally along the elongate member.

10. The system of claim 9, wherein the sheath is sized to receive the elongate member.

11. The apparatus of claim 9, wherein the elongate member operates as a dilator.

12. The apparatus of claim 9, wherein the elongate member further comprises a proximal end, a terminal end, and at least one groove extending longitudinally from the proximal end to proximate the terminal end.

13. The apparatus of claim 10, the elongate member further comprising a proximal end and a distal end, and a lock attached to the proximal end, the lock being configured to lock the introducer sheath to the inner member.

14. The apparatus of claim 10, the introducer sheath further comprising a distal end and a proximal end, the proximal end defining a handle.

15. The apparatus of claim 14, wherein the handle is adapted to be fractured into two pieces.

16. The apparatus of claim 9, the introducer sheath further comprising at least one longitudinally extending perforation along which the sheath can be split.

* * * * *